United States Patent
Chernich et al.

(10) Patent No.: US 12,251,190 B2
(45) Date of Patent: Mar. 18, 2025

(54) NIRAF CALIBRATION SHEATH PHANTOM

(71) Applicant: Canon U.S.A., Inc., Melville, NY (US)

(72) Inventors: Emily Chernich, Somerville, MA (US); Christopher Brushett, Cambridge, MA (US)

(73) Assignee: Canon U.S.A., Inc., Melville, NY (US)

( * ) Notice: Subject to any disclaimer, the term of this patent is extended or adjusted under 35 U.S.C. 154(b) by 149 days.

(21) Appl. No.: 18/046,452

(22) Filed: Oct. 13, 2022

(65) Prior Publication Data
US 2024/0122481 A1    Apr. 18, 2024

(51) Int. Cl.
*A61B 5/00*    (2006.01)

(52) U.S. Cl.
CPC .......... *A61B 5/0066* (2013.01); *A61B 5/0084* (2013.01)

(58) Field of Classification Search
CPC ............................ A61B 5/0084; A61B 5/0066
See application file for complete search history.

(56) References Cited

U.S. PATENT DOCUMENTS

| | | | |
|---|---|---|---|
| 7,288,759 B2 | 10/2007 | Frangioni et al. | |
| 8,100,893 B2 | 1/2012 | Dadisman | |
| 8,535,221 B2 | 9/2013 | Saito | |
| 8,836,939 B2 | 9/2014 | Gono | |
| 9,316,581 B2 | 4/2016 | Mander et al. | |
| 9,864,140 B2 | 1/2018 | Adler et al. | |
| 10,094,768 B2 | 10/2018 | Wijbrans et al. | |
| 10,952,616 B2 | 3/2021 | Watanabe | |
| 11,147,453 B2 | 10/2021 | Yamada et al. | |
| 2014/0005553 A1 | 1/2014 | Ryan et al. | |
| 2016/0144162 A1 | 5/2016 | Erdman | |
| 2020/0155004 A1 | 5/2020 | Kim et al. | |

FOREIGN PATENT DOCUMENTS

WO    WO-2018175878 A1 *    9/2018    ........... A61B 5/0066

OTHER PUBLICATIONS

Giovanni, "First-In-Human Dual-Modality OCT and Near-Infrared Autofluorescence Imaging of Coronary Artery Disease", Nov. 1, 2017 (Year: 2017).*
Lambros Athanasiou, et al., Intracoronary near infrared autofluorescence signal calibration, 2020 42nd Annual International Conference of the IEEE Engineering in Medicine & Biology Society (EMBC), 2020.

* cited by examiner

*Primary Examiner* — Maurice C Smith
(74) *Attorney, Agent, or Firm* — Canon U.S.A., Inc., IP Division

(57) ABSTRACT

A multimodality system includes first and second modalities, an optical probe, a detector, and a sheath with a known fluorescence phantom, wherein the phantom would be used for calibration of the catheter providing accurate NIRAF values to the user using the sheath phantom to calibrate an optical probe's measured NIRAF signal to the known fluorescence of the phantom.

18 Claims, 3 Drawing Sheets

NIRAF CALIBRATION SHEATH PHANTOM

BACKGROUND

The disclosure of this patent application relates generally to optical imaging, and in particular it relates to a multimodality imaging system for imaging bodily lumens of a subject and methods thereof for calibrating the system. More specifically, the subject innovation relates to methods for calibrating a catheter's fluorescence collection before use.

Fiber-based optical coherence tomography (OCT) probes, such as catheters and endoscopes, have been developed to access and image internal organs of humans and animals, and are now commonly used in various medical fields. OCT is a medical imaging technique for non-invasive imaging based on low-coherence interferometry employing near-infrared light. The OCT device produces three-dimensional (3D) images, with a resolution typically of a few microns. Spectral-domain OCT (SD-OCT) is a form of OCT in which the interferometric signal between a reference beam and the back-scattered component of a sample (probe) beam reflected from a sample is split into its frequency components by a dispersive device and collected by an optical detector (line camera). The collected data contains the spectral information of the backscattered signal. This spectral data can be transformed to the spatial domain to obtain a one-dimensional (1D) spatial distribution, referred to as an A-scan, representative of the scattering properties of the sample. Scanning the sample beam across the sample produces a series of adjacent A-scans which can then be used to create a two-dimensional (2D) tomogram, called a B-scan. A volume representation can be acquired by further scanning the sample beam in a third direction (depth) of the sample to collect a series of B-scans that covers the three-dimensional (3D) volume of interest.

An OCT catheter, which generally comprises a sheath, a coil and an optical probe, is navigated through a lumen, by manual or automatic control. In order to acquire cross-sectional images of tubes and cavities such as vessels, esophagus and nasal cavity, generally referred to as "bodily lumens", the optical probe is rotated with a fiber optic rotary joint (FORJ). In addition, the optical probe is simultaneously moved (translated) longitudinally during the rotation so that images are obtained in a helical scanning pattern. This longitudinal movement is most commonly performed by mechanically pulling the tip (distal end) of the probe back towards the proximal end and therefore this process is referred to as a "pullback" operation. The rotation and translation movements of the OCT catheter scans the optical probe helically inside the bodily lumen, and produces a series of adjacent helical A-scans of the sample which can then be used to create a helical two-dimensional (2D) tomogram. Moving the catheter in a third direction within the bodily lumen (changing the distance of the catheter with respect to the wall of the lumen) allows the collection of a series of B-scans which can be combined to form a three-dimensional (3D) image of the sample of interest.

Conventionally, while techniques such as OCT as well as other imaging techniques including intravascular ultrasound (IVUS) have been well established as being capable of visualizing morphologic features and depth of bodily lumens, these techniques have not been shown to identify chemicals/molecules associated with the health status of such morphologic features. In particular, the high scattering nature of bodily lumens and liquids contained therein (e.g., blood) prevent OCT from identifying important health-related parameters of imaged samples. However, determining the functional properties as well as chemical and molecular composition of tissues is as important as the structure revealed by the backscattered intensity. In recent years, to compliment this perceived deficiency of OCT, it has been proposed to add a secondary modality to OCT. Using a second imaging modality such as near-infrared autofluorescence (NIRAF) or near-infrared fluorescence (NIRF) spectroscopy with OCT has the potential to improve imaging and diagnosis results.

Intravascular fluorescence is a catheter-based molecular imaging technique that uses near-infrared fluorescence to detect artery wall autofluorescence (NIRAF) or induced fluorescence (NIRF) generated by molecular agents injected intravenously. Intravascular fluorescence typically uses near-infrared laser-light to stimulate fluorescence emission (autofluorescence) of particular plaque components formed on a vessel wall, or to generate fluorescence from molecular- or cellular-specific agents previously injected into a vessel or artery. Fluorescence detection can be obtained by integration over a short period of time of the emitted intensity based on the fluorescence life-time (of the particular plaque component or molecular agent), or by analyzing the spectral shape of emitted fluorescence (fluorescence spectroscopy). Imaging catheters contain an optical fiber and related optics to deliver and collect light to and from the inner lumen of a body. Therefore, a multimodality device including OCT or IVUS and NIRAF/NIRF imaging elements have been recently proposed.

NIRAF detection used as a second imaging modality with OCT has the potential to improve diagnosis of necrotic core lesions and other parameters. To improve image accuracy and diagnosis, the detected OCT and NIRAF signals need to be properly synchronized and calibrated. State of the art calibration for NIRAF signal involves calibrating for the detected signal as a function of distance between the catheter and blood vessel wall. However, calibrating the detected NIRAF/NIRF signal using distance alone does not consider other factors that affect the signal. The detected NIRAF/NIRF signal is also a function of the angle between the optical axis of the excitation light and the normal line to the sample surface, among other factors. Without correction for the angle, the NIRAF data will be less accurate and the desired improvement in imaging and diagnosis may not be achieved.

Various exemplary calibrations methods for a catheter include U.S. Patent Publication No. 2016/0144162 to Erdman et al., wherein the invention relates to a coupler assembly for catheters having force-sensing capabilities. Erdman includes a mechanical coupler for coupling a catheter shaft and distal tip sensing components. Such a system may be used with catheters for visualization, mapping, ablation, and/or other methods of diagnosis and treatment of tissue.

Another example, detailed in U.S. Pat. No. 8,100,893 to Dadisman, teaches an assembly including a catheter body, a housing and a detector, as well as methods for providing and calibrating a catheter supported within the housing.

Finally U.S. Pat. No. 7,288,759 to MacLaurin et al., is based, in part, on the discovery that by combining certain components one can generate a tissue-like phantom that mimics any desired tissue, is simple and inexpensive to prepare, and is stable over many weeks or months. In addition, new multi-modal imaging objects (e.g., beads) can be inserted into the phantoms to mimic tissue pathologies, such as cancer, or merely to serve as calibration standards. These objects can be imaged using one, two, or more (e.g., four) different imaging modalities (e.g., x-ray computed tomography (CT), positron emission tomography (PET), single photon emission computed tomography (SPECT), and near-infrared (NIR) fluorescence) simultaneously.

However, none of the existing literature provides a solution or method for calibration, while accounting for the catheter's measurement having a linear response to fluorescence but a variability in the slope of the linearity.

SUMMARY

The present patent application aims to improve on the above-described state of the art.

More specifically, the subject application provides an optical coherence tomography apparatus, comprising an optical probe having a first light to illuminate a sample, a detector for detecting a fluorescence of reflection of the first light for illuminating the sample, and a sheath configured to allow the optical probe to travel longitudinally through the sheath to perform a pullback, wherein the sheath has a fluorescent coating on at least a portion of the sheath surface for detection by the detector.

In other embodiments, the fluorescent coating on the sheath is of known fluorescence, and furthermore, the fluorescent coating may be used to calibrate a NIRAF linear response.

In yet another embodiment, the fluorescent coating may perpendicular to the length of the sheath, or parallel to the length of the sheath, or other combination therefrom.

Is it further contemplated that the fluorescent coating may be configured at a distal end of the sheath, the proximal end of the sheath, or both.

It is also an embodiment of the subject disclosure to incorporate a second fluorescent coating on the sheath that is different than the fluorescent coating, and may or may not have a different known fluorescence.

The subject disclosure also teaches a method for optical coherence tomography, comprising: providing an optical coherence tomography apparatus, comprising: an optical probe having a first light to illuminate a sample; a detector for detecting a fluorescence of reflection of the first light for illuminating the sample; and a sheath configured to allow the optical probe to travel longitudinally through the sheath to perform a pullback, wherein the method includes positioning the optical coherence tomography apparatus adjacent to the sample; illuminating the sample using the optical probe; and detecting the fluorescence of reflection from the sample.

This method may further include a fluorescent coating on at least a portion of the sheath surface for detection by the detector.

The method may also include performing a pullback of the optical coherence tomography apparatus to illuminate the sample in a three-dimensional state.

It is further contemplated that the method comprise performing a pullback of the optical coherence tomography apparatus to detect the fluorescence of reflection of the sample in a three-dimensional state.

Further features and advantageous of the invention will become apparent to those skilled in the art from the following description of exemplary embodiments with reference to the attached drawings.

DETAILED DESCRIPTION

Figure 1:
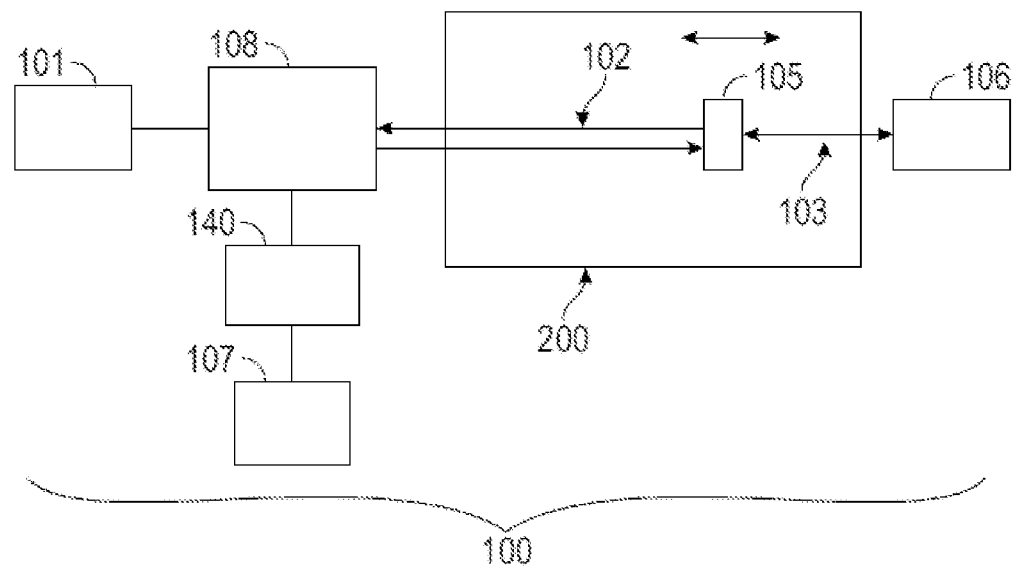
FIG. 1 is a diagram showing an embodiment of a system which can utilize a common path OCT technique with optical probe applications in accordance with one or more embodiment of the subject apparatus, method or system.

In the following description, reference is made to the accompanying drawings which are illustrations of embodiments in which the disclosed invention may be implemented and practiced. It is to be understood, however, that those skilled in the art may develop other structural and functional modifications without departing from the novelty and scope of the instant disclosure. In referring to the description, specific details are set forth in order to provide a thorough understanding of the examples disclosed. In other instances, well-known methods, procedures, components and circuits have not been described in detail as not to unnecessarily lengthen the present disclosure. Some embodiments of the present invention may be practiced on a computer system that includes, in general, one or a plurality of processors for processing information and instructions, random access (volatile) memory (RAM) for storing information and instructions, read-only (non-volatile) memory (ROM) for storing static information and instructions, a data storage devices such as a magnetic or optical disk and disk drive for storing information and instructions, an optional user output device such as a display device (e.g., a monitor) for displaying information to a user, an optional user input device including alphanumeric and function keys (e.g., a keyboard) for communicating information and command selections to the processor, and an optional user input device such as a pointing device (e.g., a mouse) for communicating user input information and command selections to the processor.

As will be appreciated by those skilled in the art, the present examples may be embodied as a system, method or computer program product. Accordingly, some examples may take the form of an entirely hardware embodiment, an entirely software embodiment (including firmware, resident software, micro-code, etc.) or an embodiment combining software and hardware aspects that may all generally be referred herein as a "circuit", "module" or "system". Further, some embodiments may take the form of a computer program product embodied in any non-transitory tangible medium of expression having computer-usable program code stored therein. For example, some embodiments described below with reference to flowchart illustrations and/or block diagrams of methods, apparatus (systems) and computer program products can be implemented by computer program instructions. The computer program instructions may be stored in computer-readable media that when executed by a computer or other programmable data processing apparatus causes the computer or processing apparatus to function in a particular manner, such that the instructions stored in the computer-readable media constitute an article of manufacture including instructions and processes which implement the function/act/step specified in the flowchart and/or block diagram.

The terms first, second, third, etc. may be used herein to describe various elements, components, regions, parts and/or sections. It should be understood that these elements, components, regions, parts and/or sections are not limited by these terms of designation. These terms of designation have been used only to distinguish one element, component, region, part, or section from another region, part, or section. Thus, a first element, component, region, part, or section discussed below could be termed a second element, component, region, part, or section merely for purposes of distinction but without departing from structural or functional meaning.

Exemplary embodiments are described below in more detail with reference to the several drawings where like reference numerals refer to like parts.

Figure 7:
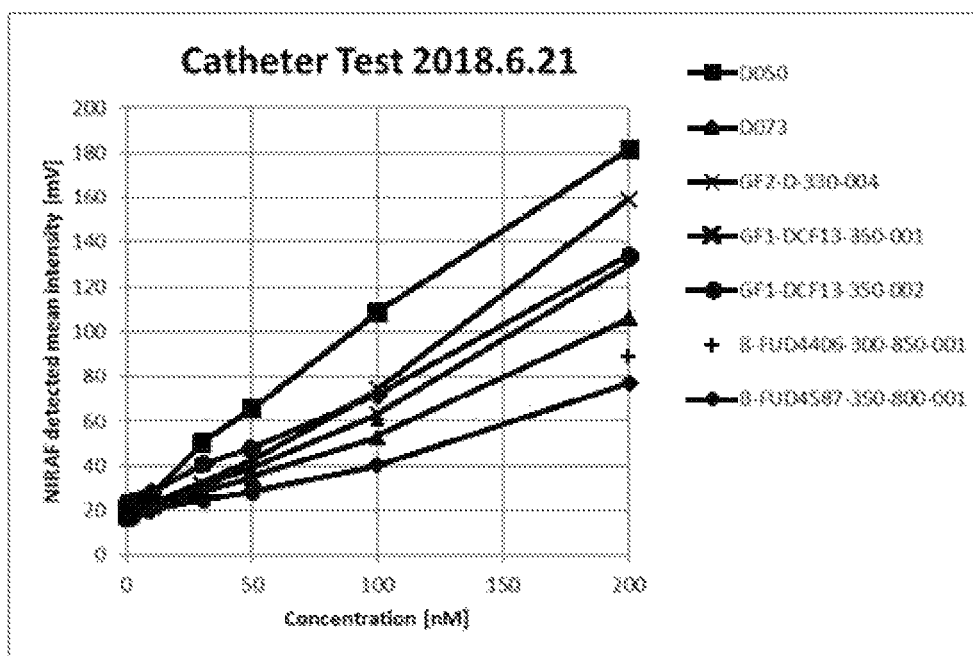
FIG. 7 depicts a graph of seven catheters tested in accordance with one or more embodiment of the subject innovation.

In operating various catheters, Applicant noted that each catheter had a variable linearity to fluorescence, which would lead to the NIRAF signal being missed or incorrect, misinforming results of fluorescence in pullback. As seen in FIG. 7, shows the 7 catheters tested resulted in wide variance of NIRAF detection mean intensity, which leads to the issues at hand, and requires an elegant solution posed herein.

One exemplary solution would be to have a fluorescent calibration phantom as a segment in the catheter sheath outside the pullback region. When the catheter has an optical core which emits a wavelength of light to produce a fluorescent response. The catheter is connected to the multi-modality OCT ("MMOCT") system, and a start-up calibration sequence begins of both the OCT and NIRAF signals. The phantom has one, known fluorescence concentration, for which the system automatically calibrates to for each catheter. By way of example, the florescence of the phantom may be at 635 nm, or any other desirable value or range of values, including but not limited to: 600 nm to 680 nm, or 520 nm to 760 nm.

As depicted in FIG. 1, an interference optical system 100 (also referred to herein as "system 100" or "the system 100") operates to utilize a common path OCT technique with optical probe applications in accordance with one or more aspects of the present disclosure. The system 100 comprises a light source 101, a reference arm 102, a sample arm 103, a deflected section 108 (e.g., a collimating lens or fiber; the deflected section 108 is also referred to herein as a deflecting section 105), a reference mirror (also referred to herein as a "reference reflector", "reference reflection", "partially reflecting mirror" and a "partial reflector") 105 (which may be included in a common path probe or probe housing 200 as shown in the embodiment of FIG. 1) and at least one detector 107. The system 100 may interact with a sample, specimen or object 106, via the sample arm 103 (as schematically shown in FIG. 1). Preferably, the reference arm 102 and the sample arm 103 share a common path between the deflected section 108 and the reference reflection 105. The reference arm 102 extends between the deflected section 108 and the reference reflection 105. The sample arm 103 extends between the deflected section 108 and the sample 106, via or through the reference reflection 105.

Preferably, the deflected section 108 operates to deflect the light from the light source 101 to the common path probe or probe housing 200, and then send light received from the common path probe or probe housing 200 towards the at least one detector 107. In one or more embodiments, the deflected section 108 of the system 100 may include or may comprise one or more common path interferometers or optical interference systems that operate as described herein, including, but not limited to, a circulator, a beam splitter, an isolator, a coupler (e.g., fusion fiber coupler), a partially severed mirror with holes therein, a partially severed mirror with a tap, etc. In one or more embodiments, the common path interferometer or the common path optical interference system may include one or more components of the system 100, such as, but not limited to, one or more of the light source 101, the reference arm 102, the sample arm 103, the deflected section 108 and/or the reference reflection 105.

In one or more embodiments, the reference reflector or reference reflection 105 is preferably disposed in the system 100 such that the reference reflector or reference reflection 105 at least one of: (i) resides in the collimation field or path (e.g., in a partially or wholly collimated field or path) and (ii) is normal (or substantially normal) or perpendicular (or substantially perpendicular) to an optic axis (e.g., an axis along which there is, or is some degree of, rotational symmetry in an optical system; an axis that defines a path along which light from the light source 101 spreads through an optical system; an axis that defines a path along which there is, or is some degree of, rotational symmetry in an optical system (such as, but not limited to, the system 100, one of the probes 200, 200a, etc.); an axis along a core of an optical fiber (see e.g., fiber 201 as shown in any of FIG. 2); an axis defining a path passing through a collimation field and along which there is, or is some degree of, rotational symmetry. In one or more embodiments, the reference arm 102 overlaps with the sample arm 103, and the reference arm 102 is spaced away from the sample 106. In one or more embodiments, the reference reflection 105 may include an optical coating to optimize a desired reflection value for the reference reflection 105. In one or more embodiments, changing an the angle of the reference reflector or reference reflection 105 with respect to the optic axis may be used to improve or optimize the reference signal, including in situations where an optical coating or other material choice may not be at nominal design value(s). For example, when intentionally further tilting the angle of the reference reflector or reference reflection 105, preferably the further angle tilt is at least one of: 1-3 degrees, 0-2 degrees, about 1 degree to about 3 degrees, about 0 degrees to about 2 degrees.

Figure 2:
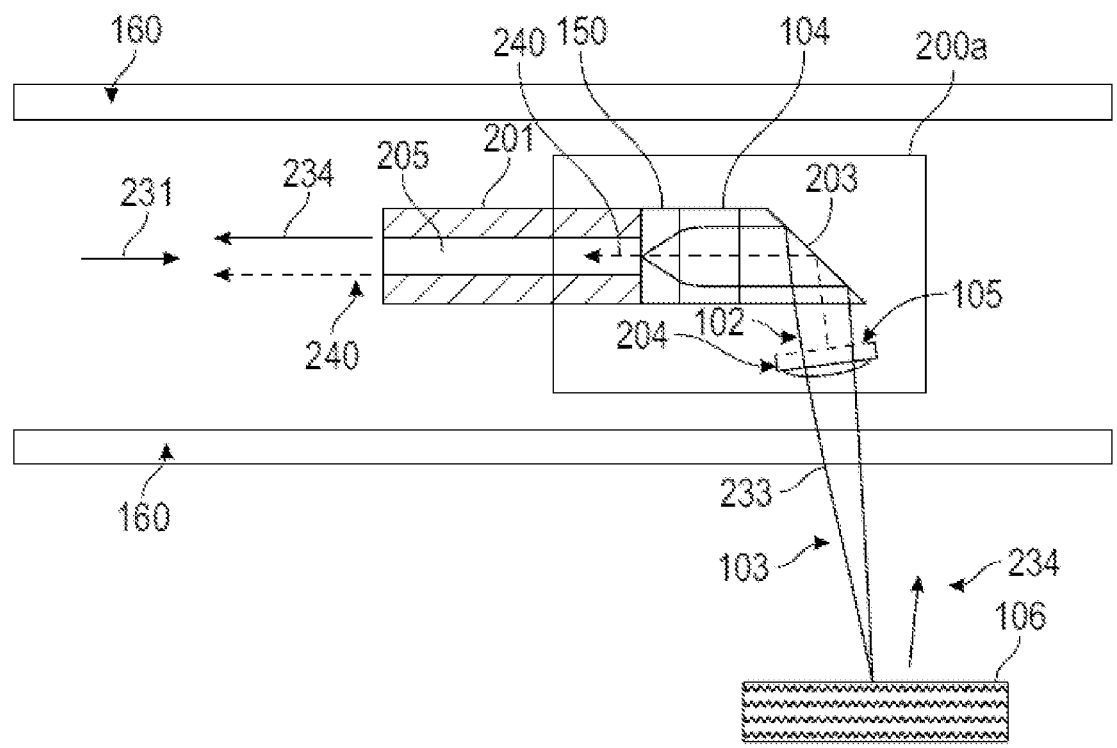
FIG. 2 shows an exemplary OCT probe positioned or located in a sheath for use with at least one OCT device or system in accordance with one or more embodiment of the subject apparatus, method or system.

In one or more embodiments, the system 100 may include, or be used with, a probe 200 having a fiber 201 attached to a collimator 104 (e.g., a collimating lens or fiber), a no core fiber (NCF) or large core multimode fiber 203 (which may be glass, plastic or any other alternative to a fiber with a core in one or more embodiments, which may be a flat or cylindrical prism, which may be a surface having a reflection that is polished flat, etc.), and a lens 204 (may be any lens, such as, but not limited to, an anamorphic lens, and may or may not be off-axis, may or may not be angled, etc.) having the reference reflection 105 disposed thereon or therein as shown in at least FIG. 2. The light from the light source 101 is sent through the system 100 (e.g., via the deflected section 108) to the collimator 104, for example, via the fiber 201. In other words, the fiber 201 operates as a signal carrying optical fiber, such as, but not limited to, a single mode fiber (SMF), a double clad fiber (DCF), a multimode fiber or other type of signal carrying fiber. In the preferred embodiment, the collimator 104 may be a mostly collimating gradient index (GRIN) lens or fiber that is fusion spliced to the signal carrying optical fiber 201. In one or more embodiments, the no core fiber (NCF) or large core multimode fiber 203 is then fusion spliced to the GRIN lens or fiber (e.g., an embodiment of the collimator 104). Preferably, the NCF 203 is polished at an angle that meets a total internal reflection (TIR) condition and is larger than 45 degrees or larger than about 45 degrees so as to minimize undesired reflection(s) from a side surface of the NCF 203 (and a catheter sheath, which may be employed with the NCF 203 in one or more embodiments of the system 100). In one or more embodiments using a catheter sheath 160, the catheter sheath 160 may affect the light detrimentally such that an astigmatism may be introduced into the lens 204 to correct or compensate for the use of the sheath. In one or more embodiments, one or more angles other than larger than 45 degrees or larger than about 45 degrees may be used (e.g., 30 degrees, 35 degrees, 40 degrees, 50 degrees, 60 degrees, or any other angle that allows the device to function as described herein) while achieving the effect of reducing or avoiding reflections from a sheath, a side surface of the NCF 203, etc. For example, in one or more embodiments, a connection component (or interface module), such as a rotary junction, may be used to connect one or more components, such as one or more components of a probe (e.g., the probe 200 or one or more components thereof (e.g., the reference reflection 105)), a needle, a capsule, a patient interface unit (e.g., interface unit 110), etc., to one or more other components, such as, an optical component, a light source (e.g., the light source 101), a deflection section (e.g., the deflection or deflected section 108), etc. For example, when the connection member or interface module is a rotary junction, the rotary junction may be at least one of: a contact rotary junction, a lenseless rotary junction, a lens-based rotary junction, or other rotary junction known to those skilled in the art.

Preferably, the lens 204 including the reference reflection 105 is placed in the path of the light to provide a desired beam profile. Such positioning of the lens 204 having the reference reflection 105 also corrects for astigmatism from a catheter sheath when the catheter sheath is used with the system 100 in one or more embodiments. The first surface of the lens 204, used as the reference reflection 105, is mostly flat and may be normal, substantially normal (e.g., ±a few degrees from normal, about 87 degrees to about 93 degrees, about 88 degrees to about 92 degrees, about 89 degrees to about 91 degrees, any angle or range of angles that would improve coupling efficiency, etc.) to the optic axis to maximize coupling efficiency of the return signal to a core 205 of the fiber 201. The angle of the reference reflection 105 may be any other angle or range of angles that improves coupling efficiency even if not normal or substantially normal to the optic axis. The reference reflection 105 can be optimized through choice of material and/or optical coating (e.g., an anti-reflective (AR) coating, a high reflection (HR) coating, a partial mirror, etc.). This type of setup allows for an improved or a maximized signal-to-noise ratio (SNR) (especially when coupling efficiency is improved or high) and is also an efficient setup when used for coherence range imaging using a common path interferometer with an adjustment section. In one or more embodiments, lens tilting of the lens 204 may be used as an additional way of adjusting coupling efficiency. The light 231 goes through the optical fiber 201, and a part of the light (a reference beam) 240 is reflected at the reference reflection 105 and sent back through the fiber 201. The rest of the light 233 illuminates the sample 106, and the reflected and/or scattered light (sample beam) 234 from the sample 106 is sent through the lens 204 and is delivered to the fiber 201 via the NCF and the collimator 104. Preferably, the sample beam 234 and the reference beam 240 are coupled, combined or recombined and go back to the deflection section 108, which thereafter sends the recombined beam towards the at least one detector 107.

The output of the one or more components of the system 100 (e.g., one or more of the probe 200, the deflected section 108, the adjustment section 140, etc.) is acquired with the at least one detector 107, e.g., such as, but not limited to, photodiodes or multi-array cameras. The at least one detector 107 measures the interference or interference patterns between the two radiation or light beams that are coupled, combined or recombined. In one or more embodiments, the reference and sample beams have traveled different optical path lengths such that a fringe effect is created and is measurable by the at least one detector 107. Electrical analog signals obtained from the output of the system 100 and/or the interferometer thereof are converted to digital signals to be analyzed with a computer, such as, but not limited to, a computer. In one or more embodiments, the light source 101 may be a radiation source or a broadband light source that radiates in a broad band of wavelengths. In one or more embodiments, a Fourier analyzer including software and electronics may be used to convert the electrical analog signals into an optical spectrum.

Embodiment 1 (Distal Fluorescent Sheath Embodiment, Fundamental Embodiment)

Figure 3:
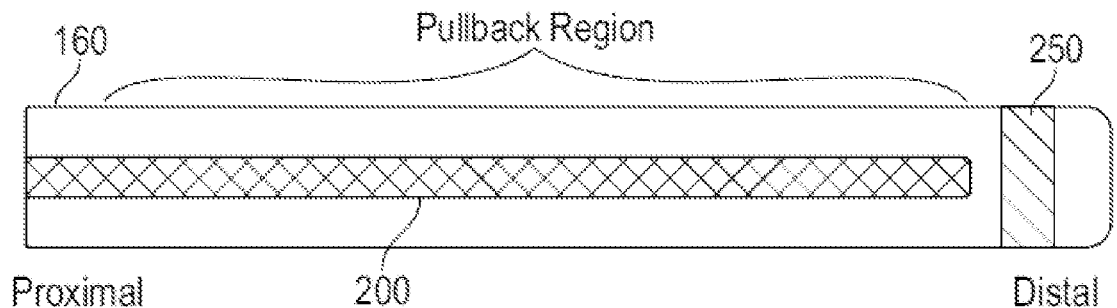
FIG. 3 illustrates an exemplary sheath used for optical coherence tomography, according to one or more embodiment of the subject apparatus, method or system.

In this first embodiment of the subject innovation, shown in FIG. 3, the sheath 160 has a short fluorescent coating (orange line in FIG. 3) which is a phantom 250 found over the sheath 160, outside of the 80 mm pullback region distally. This phantom 250 will be used to calibrate an optical catheter's measured NIRAF signal. The probe 200 (also referred to as catheter) is connected to a system and begins a calibration cycle distal to the pullback starting position where light is emitted. The probe 200 then emits this light to the sheath 160. At a known wavelength, the fluorescent coated phantom 250 will fluoresce which can then be measured as a returning signal through the catheter 200. The phantom 250 has a known concentration but each catheter 200 may have a slightly different measured value due to variance in collection efficiency caused by alignment in manufacturing. The system 100 collects the measured value during calibration, and software determines the slope of the catheter's linear response. The system 100 will enter the linearity value into the parameter file and use it for the NIRAF calibration.

Embodiment 2 (Proximal Fluorescent Sheath Embodiment)

Figure 4:
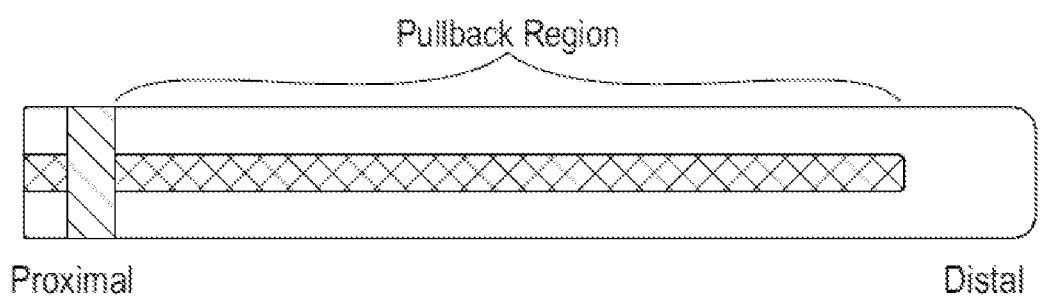
FIG. 4 provides an exemplary sheath used for optical coherence tomography, according to one or more embodiment of the subject apparatus, method or system.

As shown in FIG. 4, the sheath 160 has a short fluorescent coating or phantom 250 over the sheath 160 outside the 80 mm pullback region proximally. All calibrations steps are the same as Embodiment 1 except that it will occur in the proximal region of the sheath 160. One additional aspect is that the probe 200 can re-calibrate after each pullback before readvancing to the start position by collecting additional data just beyond the clinical pullback region, which was not possible in the first embodiment.

Embodiment 3 (Dual/Multi-Concentration Fluorescent Sheath Embodiment)

Figure 5:
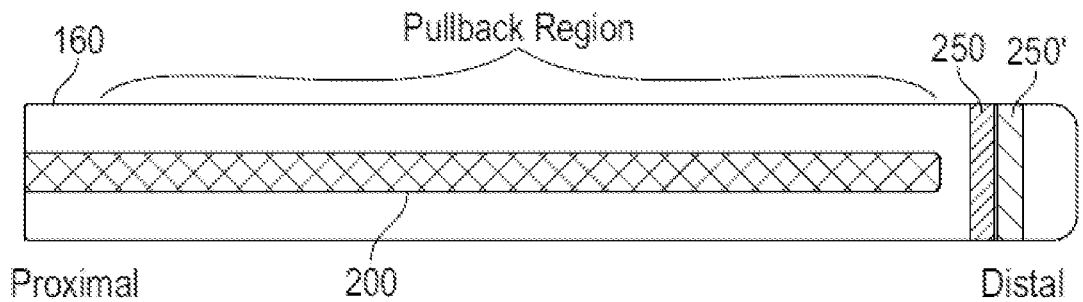
FIG. 5 illustrates an exemplary sheath used for optical coherence tomography, according to one or more embodiment of the subject apparatus, method or system.

In this embodiment, depicted in FIG. 5, the Dual/Multi-Concentration fluorescent sheath 160 has two or more known fluorescence phantoms 250 and 250' that are located in either of the previously described locations in embodiment 1 or 2. The calibration is the same as that described in embodiments 1 or 2. The dual/multi-concentration phantom 250 and 250' will provide additional linear calibration information, allowing the system 100 to more accurately determine the catheter NIRAF response. The calibration method is the same as the method explained in embodiment 1 and 2.

Embodiment 4 (Fluorescent Sheath Stripe Embodiment)

Figure 6:
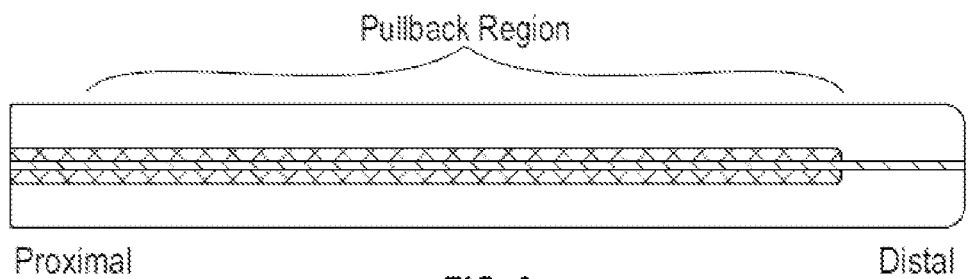
FIG. 6 depicts an exemplary sheath used for optical coherence tomography, according to one or more embodiment of the subject apparatus, method or system.

FIG. 6 shows an alternative embodiment, wherein the sheath 160 has a fluorescent stripe 250 along the length of the sheath 160 in the pullback region. This embodiment would allow for calibration in each frame of the pullback. Approximately one A-line with two known fluorescence would be visible in every frame of a pullback as a direct comparison and calibration source.

The subject innovation provides a unique and simple way to calibrate NIRAF signals for a multi-modality OCT catheter, which currently doesn't exist. Multi-modality Optical Coherence Tomography ("MMOCT") optical catheters collect fluorescence signals, but a variability in the slope of the linearity between catheters distorts the signal. This variability is largely due to collection efficiency of the NIRAF signal which is largely impacted by the optical alignment of each catheter. By providing a simple and unique method for calibration, each catheter would provide accurate NIRAF values to the user. A sheath phantom will be used to calibrate an optical catheter's measured NIRAF signal to the known fluorescence of the phantom. The system collects the measured value during calibration and software determines the slope of the catheter's linear response, saves that value into the parameter file, and can apply that value to adjust NIRAF measured values for the most accurate measurements.

While the present patent application has been described with reference to exemplary embodiments, it is to be understood that the invention is not limited to the disclosed exemplary embodiments. The scope of the following claims is to be accorded the broadest interpretation so as to encompass all possible modifications and equivalent structures and functions. To that end, it must be noted that the terminology used herein is for the purpose of describing particular embodiments only and is not intended to be limiting.

As used herein, the singular forms "a", "an", and "the" are intended to include the plural forms as well, unless the context clearly indicates otherwise. It should be further understood that the terms "includes" and/or "including", "comprises" and/or "comprising", "consists" and/or "consisting" when used in the present specification and claims, specify the presence of stated features, integers, steps, operations, elements, and/or components, but do not preclude the presence or addition of one or more other features, integers, steps, operations, elements, components, and/or groups thereof not explicitly stated.

It should be further noted that operations performed as method steps/processes or otherwise described herein in algorithm form are those operations requiring physical manipulations of physical quantities, which usually but not necessarily, take the form of electrical or magnetic signals capable of being stored, transferred, combined, transformed, compared, and otherwise manipulated electronically. Therefore, unless specifically stated otherwise, it will be apparent to those skilled in the art that throughout the above description, discussions utilizing terms such as "processing" or "computing" or "displaying" or "calculating" or "comparing, "calibrating" "generating" or "determining" and the like, refer to the action and processes of a computer system, or similar electronic component, that manipulates and transforms data represented as physical (electronic) quantities within the computer system's registers and memories into other data similarly represented as physical quantities within the computer system memories or registers or other such information storage, transmission, or display device.

The invention claimed is:

1. An apparatus, comprising:
    an optical probe having a first light to illuminate a sample;
    a detector for detecting a fluorescence of reflection of the first light for illuminating the sample;
    a sheath configured to allow the optical probe to travel longitudinally through the sheath to perform a pullback,
    wherein the sheath has a fluorescent coating of known emitted fluorescence or known range of emitted fluorescence on at least a portion of the sheath surface for detection by the detector, and
    a processor configured to
        receive an emitted fluorescence measurement value from the fluorescent coating
        determine a slope of a linear response for the emitted fluorescence measurement value, and
        use the slope of a linear response to calibrate a fluorescence linear response.

2. The apparatus of claim 1, wherein the fluorescent coating is perpendicular to the length of the sheath.

3. The apparatus of claim 1, wherein the fluorescent coating is parallel to the length of the sheath.

4. The apparatus of claim 1, wherein the fluorescent coating is configured at a distal end of the sheath and is outside of a clinical pullback region of the optical probe.

5. The apparatus of claim 1, wherein the fluorescent coating is configured at a proximal end of the sheath and is outside of a clinical pullback region of the optical probe.

6. The apparatus of claim 1, further comprising a second fluorescent coating different than the fluorescent coating.

7. A method for optical coherence tomography, comprising:
    providing an optical coherence tomography apparatus, comprising:
        an optical probe having a first light to illuminate a sample;
        a detector for detecting a fluorescence of reflection of the first light for illuminating the sample; and
        a sheath configured to allow the optical probe to travel longitudinally through the sheath to perform a pullback,
    positioning the optical coherence tomography apparatus adjacent to the sample;
    illuminating the sample using the optical probe; and
    detecting the fluorescence of reflection from the sample;
        wherein the sheath has a fluorescent coating having a known fluorescence or known range of fluorescence on at least a portion of the sheath surface for detection by the detector, and
        wherein the fluorescent coating is used to calibrate a NIRAF linear response.

8. The method of claim 7, further comprising performing a pullback of the optical coherence tomography apparatus to illuminate the sample in a three-dimensional state.

9. The method of claim 7, further comprising performing a pullback of the optical coherence tomography apparatus to detecting the fluorescence of reflection of the sample in a three-dimensional state.

10. The method of claim 7, wherein the fluorescent coating is perpendicular to the length of the sheath.

11. The method of claim 7, wherein the fluorescent coating is parallel to the length of the sheath.

12. The method of claim 7, wherein the fluorescent coating is configured at a distal end of the sheath.

13. The method of claim 7, wherein the fluorescent coating is configured at a proximal end of the sheath.

14. The method of claim 7, further comprising a second fluorescent coating different than the fluorescent coating.

15. An apparatus, comprising:
- an optical probe having a first light to illuminate a sample;
- a detector for detecting a fluorescence of reflection of the first light for illuminating the sample;
- a sheath configured to allow the optical probe to travel longitudinally through the sheath to perform a pullback,
- wherein the sheath has a fluorescent coating of known emitted fluorescence or known range of emitted fluorescence configured at either a distal end of the sheath or a proximal end of the sheath and outside of a clinical pullback region of the optical probe for detection by the detector, and
- wherein the fluorescent coating is configured for calibration of a fluorescence linear response.

16. The apparatus of claim 15, wherein the fluorescent coating is perpendicular to the length of the sheath.

17. The apparatus of claim 15, wherein the fluorescent coating is parallel to the length of the sheath.

18. The apparatus of claim 15, further comprising a second fluorescent coating different than the fluorescent coating.

* * * * *